United States Patent [19]
Löser et al.

[11] Patent Number: 5,827,892
[45] Date of Patent: Oct. 27, 1998

[54] USE OF DROLOXIFENE FOR THE TREATMENT OF CARDIOVASCULAR DISEASES

[75] Inventors: Roland Löser, Feldafing; Michael Schliack, München, both of Germany; David D. Thompson, Gales Ferry, Conn.

[73] Assignee: Pfizer Inc., New York, N.Y.

[21] Appl. No.: 605,131

[22] PCT Filed: May 26, 1995

[86] PCT No.: PCT/IB95/00403

§ 371 Date: Mar. 13, 1996

§ 102(e) Date: Mar. 13, 1996

[87] PCT Pub. No.: WO96/02242

PCT Pub. Date: Feb. 1, 1996

Related U.S. Application Data

[63] Continuation-in-part of Ser. No. 276,969, Jul. 19, 1994, Pat. No. 5,441,986.

[51] Int. Cl.$^6$ .................................................. A61K 31/135
[52] U.S. Cl. .................................................... 514/648
[58] Field of Search ..................................... 514/651, 648

[56] References Cited

U.S. PATENT DOCUMENTS

| | | | |
|---|---|---|---|
| 5,047,431 | 9/1991 | Schickaneder et al. | 514/648 |
| 5,071,956 | 12/1991 | Wautier | 530/329 |
| 5,254,594 | 10/1993 | Niikura et al. | 514/648 |
| 5,262,319 | 11/1993 | Iwata et al. | 435/240.2 |
| 5,384,332 | 1/1995 | Fontana | 514/648 |
| 5,426,123 | 6/1995 | Fontana | 514/651 |
| 5,455,275 | 10/1995 | Fontana | 514/648 |

OTHER PUBLICATIONS

Stedman's Medical Dictionary 24th ED, Williams & Wilkins, Balto, MD, 1983, p. 1278.

Tietz, N. W. *Clinical Guide to Laboratory Tests* (1983) pp. 114–117.

Solmssen, U.V., "Synthetic Estrogens and the Relation Between Their Structure and Their Activity,". *Chemical Reviews*, 37 526–7 (1945).

Wiseman, H. et al., "Droloxifene (3–hydroxytamoxifen) has membrane antioxidant ability: potential relevance to its mechanism of therapeutic action in breast cancer," Cancer Letters, 66 (1992) 61–68.

Gill–Sharma, M.K., et al., "Effects of Tamoxifen on the Fertility of male Rats", The Prostate 23, 245–62 (1993).

Neubauer, B.L., et al., "Endocrine and Antiprostatic Effects of Raloxifene (LY156758) in the Male Rat", J. Reprod. & Fertility 99, 395–402 (1993).

Faulkner, et al., "Regional and Total Body Bone Mineral Content, Bone Mineral Density, and Total Body Tissue Composition in Children 8–16 Years of Age" Calcified tissue 53:7–12(1993).

Jones, Robert C., "The Effect of a Luteinizing Hormone Releasing (LRH) Agonist (Wy–40,972), Levonorgestrel, Danazol and Ovariectomy on Experimental Endometriosis in the Rat" Acta Endocrinologica 106, 282–8 (1984).

Grainger, David J., et al. Biochem J. 294, 109–112 "Tamoxifen decreases the rate of proliferation of rat vascular smooth–muscle cells in culture by inducing production of transforming growth factor β".

Knabbe, C., et al. Am. J. Clin. Oncol (CCT), vol. 14, Suppl. 2, 1991, p. S15–S20. "Induction of Transforming Growth Factor β by the Antiestrogens Droloxifene, Tamoxifen, and Toremifene in MCF–7 Cells".

Pritchard, K., "Summary", Am. J. Clin. Oncol., S62–S63 (1991).

Cypriani, B., et al., "Role of Estrogen Receptors and Anti-estrogen Binding Sites in an Early Effect of Antiestrogens, the Inhibition of Cholesterol Biosynthesis", J. Steroid Biochem., 763–771, (1988).

Bruning, P.F., "Droloxifene, A New Anti–oestrogen in Post-menopausal Advanced Breast Cancer: Preliminary Results of a Double–blind Dose–finding Phase II Trial", Eur F Cancer, 1404–1407 (1992).

Wiseman, H., et al., "Tamoxifen Inhibits Lipid Peroxidation in Cardiac Microsomes", Biochemical Pharmacology, 1851–1855 (1993).

Love, R. R., "Effects of Tamoxifen on Cardiovascular Risk Factor in Postmenopausal Women", Annals of Internal Medicine, 115, 860–864 (1991).

Schwartz, J. et al., "Clinical Pharmacology of Estrogens: Cardiovascular Actions and Cardioprotective Benefits of Replacement Therapy in Postmenopausal Women", J. Clin. Pharmacol, 35:314–329 (1995).

Bierman, E.L., "Atherosclerosis and other forms of arteriosclerosis", National Center of Health Statistics, 1106–1110 (1989).

Wiseman, H., "Tamoxifen: New Membrane–Mediated Mechanisms of Action and Therapeutic Advances", Tips, 83–89 (1994).

Wiseman, H., et al., "Droloxifene (3–hydroxytamoxifen) has membrane antioxidant ability: potential relevance to its mechanism of therapeutic action in breast cancer", Cancer Letters, 66 61–68 (1992).

Steinberg, D., et al., "Modifications of Low–Density Lipoprotein that Increase its Atherogenicity", The New England Journal of Medicine, 915–924 (1989).

Wiseman, H., et al., Protective actions of tamoxifen and 4–hydroxytamoxifen against oxidative damage to human low–density lipoproteins: a mechanism accounting for the cardioprotective action of tamoxifen?, Biochem, J. 292 635 (1993).

*Primary Examiner*—Jerome D. Goldberg
*Attorney, Agent, or Firm*—Peter C. Richardson; Gregg C. Benson; Mervin E. Brokke

[57] ABSTRACT

Use of droloxifene in the treatment of cardiovascular diseases.

2 Claims, No Drawings

USE OF DROLOXIFENE FOR THE TREATMENT OF CARDIOVASCULAR DISEASES

CROSS REFERENCE TO RELATED APPLICATIONS

This is a continuation-in-part of U.S. application Ser. No. 08/276,969 filed Jul. 19, 1994, now U.S. Pat. No. 5,441,986, and a 371 of PCT/IB95/0043 filed May 26, 1995.

FIELD OF THE INVENTION

This invention relates to remedies for cardiovascular diseases comprising, as active ingredient, droloxifene having the chemical structure represented by the following formula,

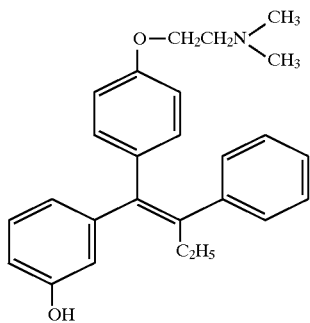

or a pharmaceutically acceptable salt thereof.

BACKGROUND OF THE INVENTION

Droloxifene is a known compound disclosed in U.S. Pat. No. 5,047,431 in which it is disclosed as an anti-tumor agent, particularly for treatment and prevention of cancer of the breast. Droloxifene is also useful for the relief of bone diseases caused by the deficiency of estrogen or the like, which are often observed in women after menopause or those with the ovaries removed. U.S. Pat. No. 5,254,594.

Gill-Sharma, et al., *J. Reproduction and Fertility* (1993) 99, 395, disclose that tamoxifen at 200 and 400 mg/kg/day reduces the weights of the testes and secondary sex organs in male rats.

Neubauer, et al., *The Prostate* 23:245 (1993) teach that raloxifene treatment of male rats produced regression of the ventral prostate.

SUMMARY OF THE INVENTION

This invention provides a method for treating a condition or disease selected from cardiovascular disease or hypercholesterolemia in mammals which comprises administering to said mammal an amount of droloxifene or a pharmaceutically acceptable salt thereof which is effective in treating said condition or disease.

DETAILED DESCRIPTION OF THE INVENTION

The preparation of droloxifene (1-[4'-(2-dimethylaminoethoxy)phenyl]-1-(3'-hydroxyphenyl)-2-phenylbut-1-ene) and pharmaceutically acceptable salts thereof is described in U.S. Pat. No. 5,047,431 which is incorporated herein by reference.

As used in this application, "prostatic disease" means benign prostatic hyperplasia or prostatic carcinoma. "Cardiovascular disease" means hypercholesterolemia and atherosclerosis. "Treating" means curing, alleviating the symptoms of or preventing the onset of a disease or condition.

The remedies for the cardiovascular diseases, hypercholesterolemia and atherosclorosis of this invention comprise, as active ingredient, droloxifene or a salt thereof. The pharmaceutically acceptable salts of droloxifene are salts of non-toxic type commonly used, such as salts with organic acids (e.g., formic, acetic, citric, maleic, tartaric, methanesulfonic, benzenesulfonic or toluenesulfonic acids), inorganic acids (e.g. hydrochloric, hydrobromic, sulfuric or phosphoric acids), and amino acids (e.g., aspartic or glutamic acids). These salts may be prepared by the methods known to chemists of ordinary skill.

The remedies for the diseases and conditions of this invention may be administered to animals including humans orally or parenterally in the conventional form of preparations, such as capsules, microcapsules, tablets, granules, powder, troches, pills, suppositories, injections, suspensions and syrups.

The remedies for the diseases and conditions of this invention can be prepared by the methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinylpyrrolidone or aluminum stearate), a dispersing agent (e.g., hydroxypropylmethylcellulose), a diluent (e.g., water), and base wax (e.g., cocoa butter, white petrolatum or polyethylene glycol). The amount of the active ingredient in the medical composition may be at a level that will exercise the desired therapeutical effect; for example, about 1 mg to 100 mg in unit dosage for both oral and parenteral administration.

The active ingredient may be usually administered once to four times a day with a unit dosage of 0.25 mg to 100 mg in human patients, but the above dosage may be properly varied depending on the age, body weight and medical condition of the patient and the type of administration. One dose per day is preferred.

The following Examples will serve to illustrate, but do not limit the invention which is defined by the claims.

EXAMPLE 1

Effect on Prostate Weight

Male Sprague-Dawley rats, three months of age were administered by subcutaneous injection either vehicle (10% ethanol in water), estradiol (30 µg/kg), testosterone (1 mg/kg) or droloxifene citrate (10 mg/kg) daily for 14 days (n=6/group). After 14 days the animals were sacrificed, the prostate was removed and the wet prostate weight was determined. Mean weight was determined and statistical significance (p<0.05) was determined compared to the vehicle-treated group using Student's t-test.

Droloxifene citrate at 10 mg/kg/day significantly (P<0.05) decreased prostate weight compared to vehicle. Testosterone had no effect while estrogen at 30 µg/kg significantly reduces prostate weight.

These data showed that droloxifene citrate is useful in the treatment of benign prostatic hypertrophy and prostatic cancer.

EXAMPLE 2

Effect on Total Cholesterol Levels

The effect of the compound of the present invention on plasma levels of total cholesterol was measured in the following way. Blood samples were collected via cardiac puncture from anesthetized female Sprague-Dawley rats 4–6 months of age that were bilaterally ovariectomized and treated with droloxifene citrate (5 mg/kg/day, po) for 28 days or with vehicle for the same time, or sham operated. The blood was placed in tubes containing 30 µL of 5% EDTA (10 µL EDTA/1 mL of blood). After centrifugation at 2500 rpm for 10 minutes at 20° C. the plasma was removed and stored at −20° C. until assay. The total cholesterol was assayed using a standard enzymatic determination kit from Sigma Diagnostics, P. O. Box 14508, St. Louis, Mo. 61378 (Procedure No. 352). The Table that follows shows the effect of droloxifene citrate on total plasma cholesterol. Droloxifene citrate after dosing (5 mg/kg/day for 28 days, po) caused a significant drop (30% versus vehicle treated ovariectomized rats) in total plasma cholesterol.

| Effect of Droloxifene Citrate in Female Rats on Total Plasma Cholesterol | | | |
|---|---|---|---|
| | Plasma Cholesterol (mg/dl) | % Change vs SHAM + VEH | % Change vs OVX + VEH |
| SHAM + VEH | 57 | — | — |
| OVX + VEH | 112 | 96 | — |
| Droloxifene citrate (5 mg/kg/day, 28 days, po) | 78 | +36 | −30 |

The same experiment was performed on Sprague-Dawley male rats (3 month old) sham operated and orchiectomized rats treated with vehicle and droloxifene citrate (10 mg/kg/day for 14 days, po). As shown in the Table below, droloxifene citrate significantly lowered total plasma cholesterol by 48% vs sham operated and 59% vs orchiectomized vehicle treated animals.

| Effect of Droloxifene in Male Rats on Total Plasma Cholesterol | | | |
|---|---|---|---|
| | Plasma Cholesterol (mg/dl) | Change SHAM vs VEH % | Change oophEx + VEH |
| SHAM + VEH | 72 | — | — |
| orchiectomized + VEH | 91 | — | — |
| Droloxifene citrate (10 mg/kg/day, 14 days, po) + VEH | 37 | −48 | −59 |

These data show that droloxifene citrate is effective in treating cardiovascular diseases such as atherosclerosis and hypercholesteremia.

EXAMPLE 3

| Droloxifene Citrate Tablets | |
|---|---|
| Droloxifene citrate | 100 g |
| Lactose | 1190 g |
| Low substituted hydroxypropylcellulose | 250 g |
| Polyvinylpyrrolidone | 50 g |
| Magnesium stearate | 10 g |

The components listed above are mixed together by the usual method, and the mixture thus obtained is compressed into 10,000 tablets each containing 10 mg of droloxifene citrate.

We claim:

1. A method for the treatment or prevention of atherosclerosis which comprises administering to a mammal in need of such treatment an effective amount of droloxifene or a pharmaceutically acceptable salt thereof.

2. A method of claim 1 wherein said pharmaceutically acceptable salt is the citrate salt.

* * * * *